US010300274B2

(12) United States Patent
Meister et al.

(10) Patent No.: US 10,300,274 B2
(45) Date of Patent: May 28, 2019

(54) DYNAMIC STIMULATION CHANNEL SELECTION

(71) Applicant: MED-EL Elektromedizinische Geraete GmbH, Innsbruck (AT)

(72) Inventors: Dirk Meister, Innsbruck (AT); Mathias Kals, Innsbruck (AT); Peter Schleich, Telfs (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 495 days.

(21) Appl. No.: 14/488,414

(22) Filed: Sep. 17, 2014

(65) Prior Publication Data
US 2015/0080980 A1    Mar. 19, 2015

Related U.S. Application Data

(60) Provisional application No. 61/879,252, filed on Sep. 18, 2013.

(51) Int. Cl.
*A61N 1/36* (2006.01)
*A61N 1/05* (2006.01)

(52) U.S. Cl.
CPC ..... *A61N 1/36032* (2013.01); *A61N 1/36036* (2017.08); *A61N 1/0541* (2013.01)

(58) Field of Classification Search
CPC .................................. A61N 1/36032
See application file for complete search history.

(56) References Cited

U.S. PATENT DOCUMENTS

| 8,374,699 | B2 | 2/2013 | Meister et al. ............ 607/57 |
| 8,417,348 | B2 | 4/2013 | Schleich .................. 607/57 |
| 2012/0004705 | A1 | 1/2012 | James ..................... 607/57 |
| 2012/0004706 | A1* | 1/2012 | Meister ......... A61N 1/36032 607/57 |

FOREIGN PATENT DOCUMENTS

WO    WO 2011/088130 A2    7/2011

OTHER PUBLICATIONS

International Searching Authority, Authorized Officer Blaine R. Copenheaver, International Search Report and Written Opinion, PCT/US2014/055985, dated Dec. 31, 2014, 13 pages.

* cited by examiner

*Primary Examiner* — Carl H Layno
*Assistant Examiner* — Jennifer L Ghand
(74) *Attorney, Agent, or Firm* — Sunstein Kann Murphy & Timbers LLP

(57) ABSTRACT

A signal processing arrangement generates electrode stimulation signals to stimulation contacts in a cochlear implant electrode array. A signal filter bank transforms an input sound signal into band pass signals, which each represent an associated frequency band of audio frequencies. An envelope processing module processes the band pass signals in a sequence of sampling time frames, wherein for each time frame, the processing includes calculating for each band pass signal at least one signal envelope dynamic property that is changing during the time frame. A channel selection module selects one or more of the band pass signals for each time frame based on the dynamic properties to produce the electrode stimulation signals to the stimulation contacts.

7 Claims, 9 Drawing Sheets

DYNAMIC STIMULATION CHANNEL SELECTION

This application claims priority from U.S. Provisional Patent Application 61/879,252, filed Sep. 18, 2013, which is incorporated herein by reference in its entirety.

FIELD OF THE INVENTION

The present invention relates to cochlear implant systems, and more specifically, to techniques for coding electrical stimulation pulses in such systems.

BACKGROUND ART

A normal ear transmits sounds as shown in FIG. 1 through the outer ear 101 to the tympanic membrane 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

FIG. 1 also shows some components of a typical cochlear implant system which includes an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110.

Typically, this electrode array 110 includes multiple stimulation contacts 112 on its surface that provide selective stimulation of the cochlea 104. Depending on context, the stimulation contacts 112 are also referred to as electrode channels. In cochlear implants today, a relatively small number of electrode channels are each associated with relatively broad frequency bands, with each stimulation contact 112 addressing a group of neurons through an electric stimulation pulse having a charge which is derived from the instantaneous amplitude of the signal envelope within that frequency band. In some coding strategies, stimulation pulses are applied at a constant rate across all electrode channels, whereas in other coding strategies, stimulation pulses are applied at a channel-specific rate. Various specific signal processing schemes can be implemented to produce the electrical stimulation signals. Signal processing approaches that are well-known in the field of cochlear implants include continuous interleaved sampling (CIS) digital signal processing, channel specific sampling sequences (CSSS) digital signal processing (as described in U.S. Pat. No. 6,348,070, incorporated herein by reference), spectral peak (SPEAK) digital signal processing, and compressed analog (CA) signal processing.

For example, FIG. 2 shows the major functional blocks in a typical CIS signal processing system wherein band pass signals containing stimulation timing and amplitude information are assigned to stimulation electrodes. FIG. 3 shows an example of a short time period of an audio speech signal from a microphone. Preprocessor Filter Bank 201 preprocesses the initial acoustic audio signal with a bank of band pass filters, each of which is associated with a specific band of audio frequencies so that the acoustic audio signal is filtered into some M band pass signals, $B_1$ to $B_M$ where each signal corresponds to the band of frequencies for one of the band pass filters. FIG. 4 shows an acoustic microphone signal decomposed by band-pass filtering by a bank of filters into a set of signals.

The band pass signals $B_1$ to $B_M$ are input to a Stimulation Pulse Generator 202 which extracts signal specific stimulation information—e.g., envelope information, phase information, timing of requested stimulation events, etc.—into a set of N stimulation event signals $S_1$ to $S_N$, which represent electrode specific requested stimulation events. For example, channel specific sampling sequences (CSSS) may be used as described in U.S. Pat. No. 6,594,525, which is incorporated herein by reference.

Pulse Mapping Module 203 applies a non-linear mapping function (typically logarithmic) to the amplitude of the each band-pass envelope. This mapping function typically is adapted to the needs of the individual CI user during fitting of the implant in order to achieve natural loudness growth. This may be in the specific form of functions that are applied to each requested stimulation event signal $S_1$ to $S_N$ that reflect patient-specific perceptual characteristics to produce a set of electrode stimulation signals $A_1$ to $A_M$ that provide an optimal electric representation of the acoustic signal.

Patient specific stimulation is achieved by individual amplitude mapping and pulse shape definition in Pulse Shaper 204 which develops the set of electrode stimulation signals $A_1$ to $A_M$ into a set of output electrode pulses $E_1$ to $E_M$ to the stimulation contacts in the implanted electrode array which stimulate the adjacent nerve tissue.

Based on the tonotopic organization of the cochlea, each stimulation contact in the scala tympani is associated with a band pass filter of the external filter bank. Symmetrical biphasic current pulses are typically applied for stimulation. The amplitudes of the stimulation pulses are directly obtained from the compressed band pass signal envelopes. The band pass signals are sampled sequentially, and the stimulation pulses are applied in a strictly non-overlapping sequence. Thus, as a typical CIS-feature, only one electrode channel is active at one time and the overall stimulation rate is comparatively high. For example, assuming an overall stimulation rate of 18 kpps and a 12 channel filter bank, the stimulation rate per channel is 1.5 kpps. Such a stimulation rate per channel usually is sufficient for adequate temporal representation of the envelope signal. The maximum overall stimulation rate is limited by the minimum phase duration per pulse. The phase duration cannot be chosen arbitrarily short, because the shorter the pulses, the higher the current amplitudes have to be to elicit action potentials in neurons, and current amplitudes are limited for various practical reasons. For an overall stimulation rate of 18 kpps, the phase duration is 27 µs, which is near the lower limit. Each output of the CIS band pass filters can roughly be regarded as a sinusoid at the center frequency of the band pass filter which is modulated by the envelope signal. This is due to the quality factor ($Q \approx 3$) of the filters. In case of a voiced speech segment, this envelope is approximately periodic, and the repetition rate is equal to the pitch frequency.

In the existing CIS-strategy, only the signal envelopes are used for further processing, i.e., they contain the entire stimulation information. For each electrode channel, the signal envelope is represented as a sequence of biphasic pulses at a constant repetition rate. A characteristic feature of CIS is that this repetition rate (typically 1.5 kpps) is equal for all electrode channels and there is no relation to the center frequencies of the individual channels. It is intended that the repetition rate is not a temporal cue for the patient, i.e., it should be sufficiently high, so that the patient does not perceive tones with a frequency equal to the repetition rate. The repetition rate is usually chosen at greater than twice the bandwidth of the envelope signals (Nyquist theorem).

Another cochlear implant stimulation strategy that transmits fine time structure information is the Fine Structure Processing (FSP) strategy by Med-El. Zero crossings of the band pass filtered time signals are tracked, and at each negative to positive zero crossing a Channel Specific Sampling Sequence (CSSS) is started. Typically CSSS sequences are only applied on the first one or two most apical electrode channels, covering the frequency range up to 200 or 330 Hz. The FSP arrangement is described further in Hochmair I, Nopp P, Jolly C, Schmidt M, Schößer H, Garnham C, Anderson I, *MED-EL Cochlear Implants: State of the Art and a Glimpse into the Future*, Trends in Amplification, vol. 10, 201-219, 2006, which is incorporated herein by reference.

Many CI coding strategies use what is referred to as an n-of-m approach where only some number n electrode channels with the greatest amplitude are stimulated in a given sampling time frame. If, for a given time frame, the amplitude of a specific electrode channel remains higher than the amplitudes of other channels, then that channel will be selected for the whole time frame. Subsequently, the number of electrode channels that are available for coding information is reduced by one, which results in a clustering of stimulation pulses. Thus, fewer electrode channels are available for coding important temporal and spectral properties of the sound signal such as speech onset.

One method to reduce the spectral clustering of stimulation per time frame is the MP3000™ coding strategy by Cochlear Ltd, which uses a spectral masking model on the electrode channels. Another method that inherently enhances coding of speech onsets is the ClearVoice™ coding strategy used by Advanced Bionics Corp, which selects electrode channels having a high signal to noise ratio. U.S. Patent Publication 2005/0203589 describes how to organize electrode channels into two or more groups per time frame. The decision which electrode channels to select is based on the amplitude of the signal envelopes.

SUMMARY OF THE INVENTION

Embodiments of the present invention are directed to a signal processing arrangement that generates electrode stimulation signals to stimulation contacts in a cochlear implant electrode array. A signal filter bank transforms an input sound signal into band pass signals, which each represent an associated frequency band of audio frequencies. An envelope processing module processes the band pass signals in a sequence of sampling time frames, wherein for each time frame, the processing includes calculating for each band pass signal at least one signal envelope dynamic property that is changing during the time frame. A channel selection module selects one or more of the band pass signals for each time frame based on the dynamic properties to produce the electrode stimulation signals to the stimulation contacts.

There may be a pulse scaling module to weight the electrode stimulation signals based on patient-specific stimulation response characteristics. In specific embodiments, the pulse scaling module may either precede or follow the channel selection module.

The signal envelope dynamic property may specifically be a first-order time derivative or higher. In some embodiments, the channel selection module select exactly one band pass signal for each time frame based on the dynamic properties. And the channel selection module may further use band pass signal envelope amplitude to select the one or more band pass signals.

DETAILED DESCRIPTION OF SPECIFIC EMBODIMENTS

Embodiments of the present invention are directed to using higher order dynamic properties of the incoming sound signal for selection of the stimulation channels in a cochlear implant system. This provides better presentation of temporal properties of the sound signal and onset enhancement in the sound signal. Embodiments are especially capable of emphasizing speech onsets that appear during consonants and that are important for speech understanding. The described approach also provides inherent noise reduction since electrode channels with fast-changing signal envelopes will have relatively high signal-to-noise ratios (SNR) when the noise is a stationary signal. Consequently, electrode channels with high SNR and high dynamic properties will be preferably stimulated. The resulting stimulation rate also provides sound information. Periods in the sound signal with rising amplitude (onsets) get emphasized and the instantaneous stimulation rate is raised during onsets in the sound signal. Therefore, the rate of stimulation will code information about the temporal properties of the sound signal. That does not occur in CIS coding where the stimulation rate does not transfer any information.

Figure 1:
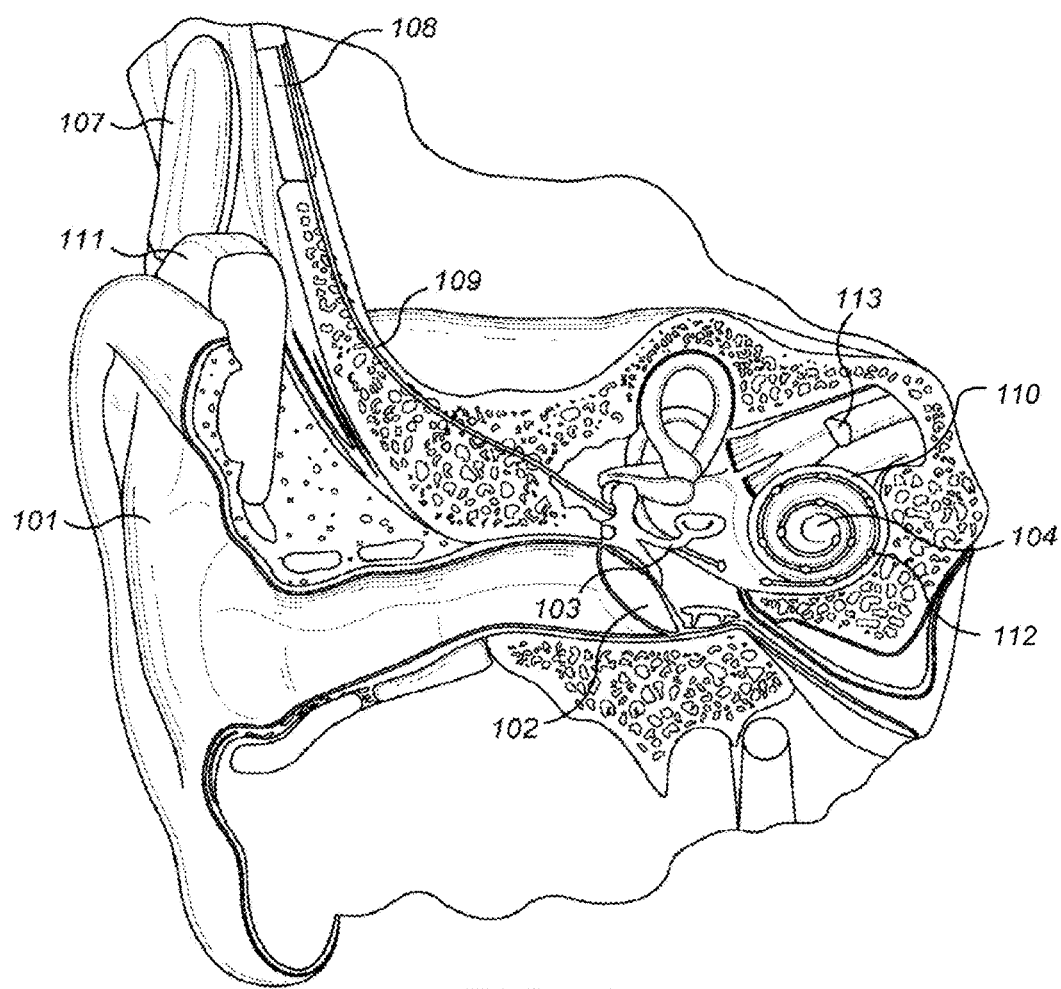
FIG. 1 shows a section view of a human ear with a typical auditory prosthesis system designed to deliver electric stimuli to the inner ear and acoustic stimuli at the ear canal.
Figure 2:
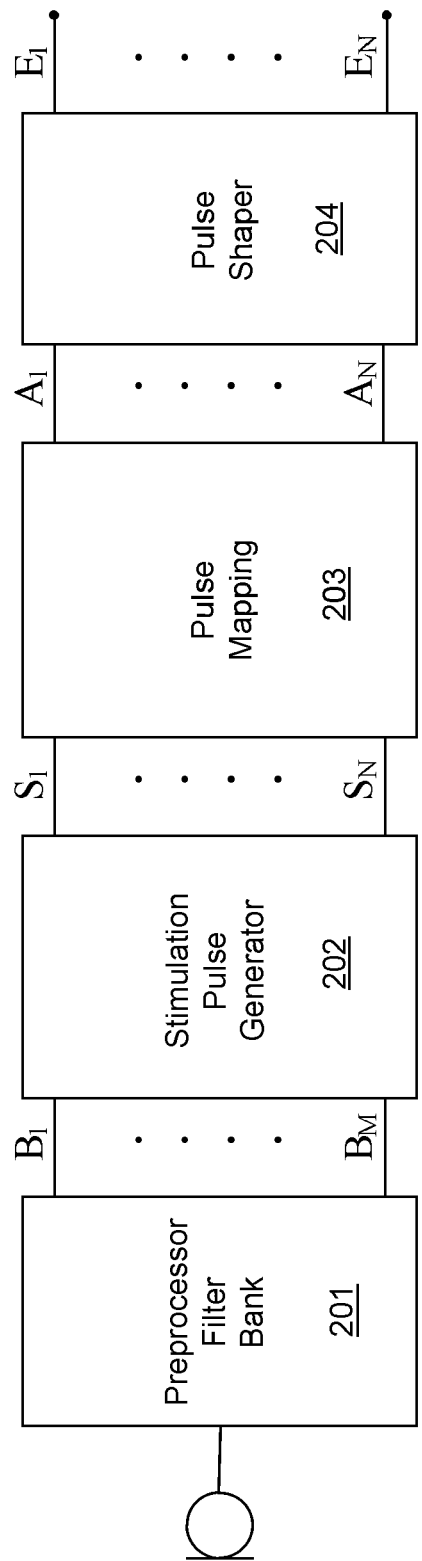
FIG. 2 shows various functional blocks in a continuous interleaved sampling (CIS) processing system.
Figure 3:
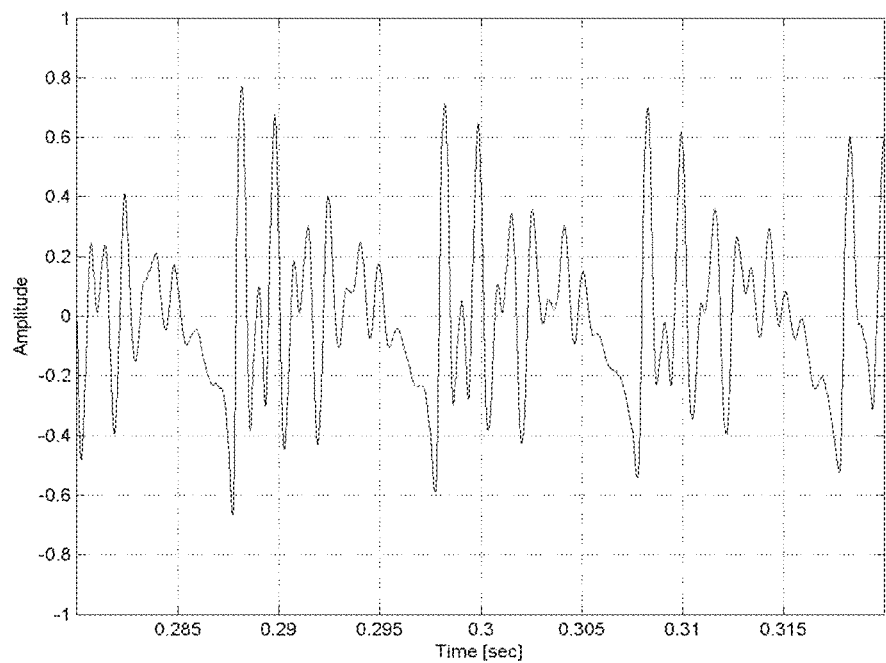
FIG. 3 shows an example of a short time period of an audio speech signal from a microphone.
Figure 4:
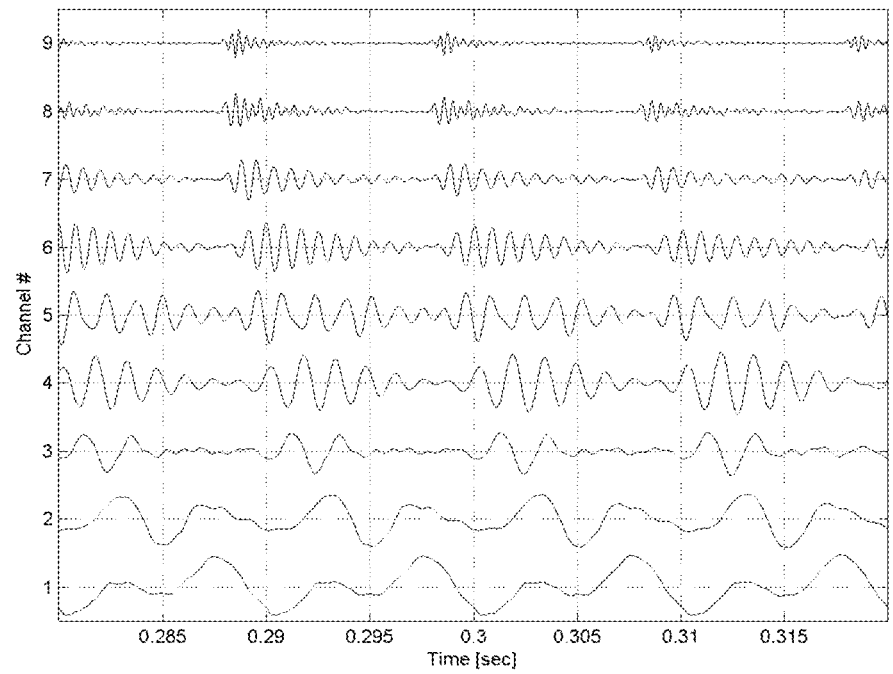
FIG. 4 shows an acoustic microphone signal decomposed by band-pass filtering by a bank of filters into a set of signals.
Figure 5:
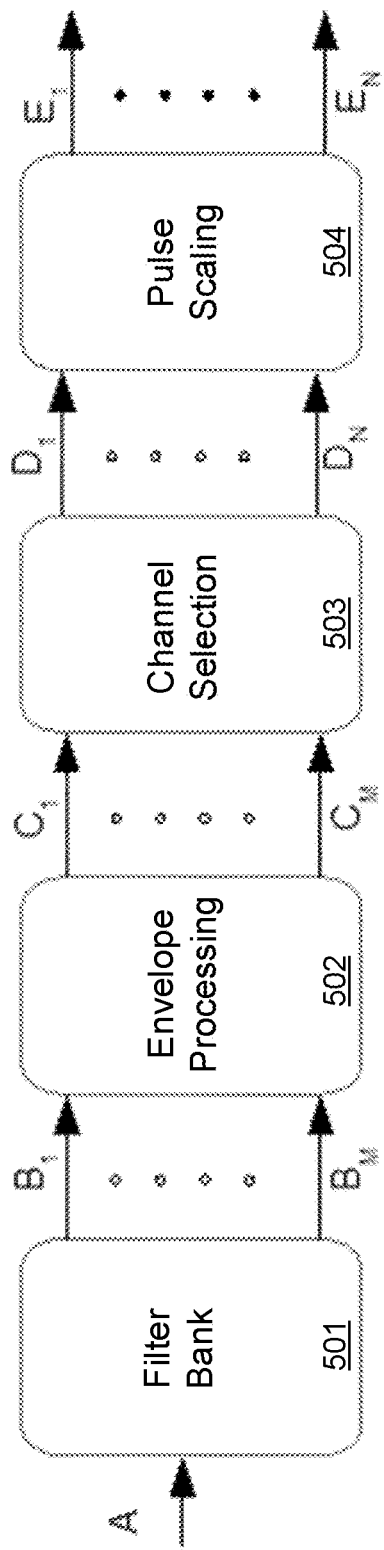
FIG. 5 shows various functional blocks in a dynamic stimulation channel selection processing system according to an embodiment of the present invention.

FIG. 5 shows various functional blocks in a dynamic stimulation channel selection processing system according to an embodiment of the present invention. A signal filter bank 501 transforms an input sound signal A into M band pass signals B that each represent an associated frequency band of audio frequencies. The signal filter bank 501 can use finite impulse response (FIR) and infinite impulse response (IIR) band pass filters, or a fast Fourier transform (FFT).

Figure 9:
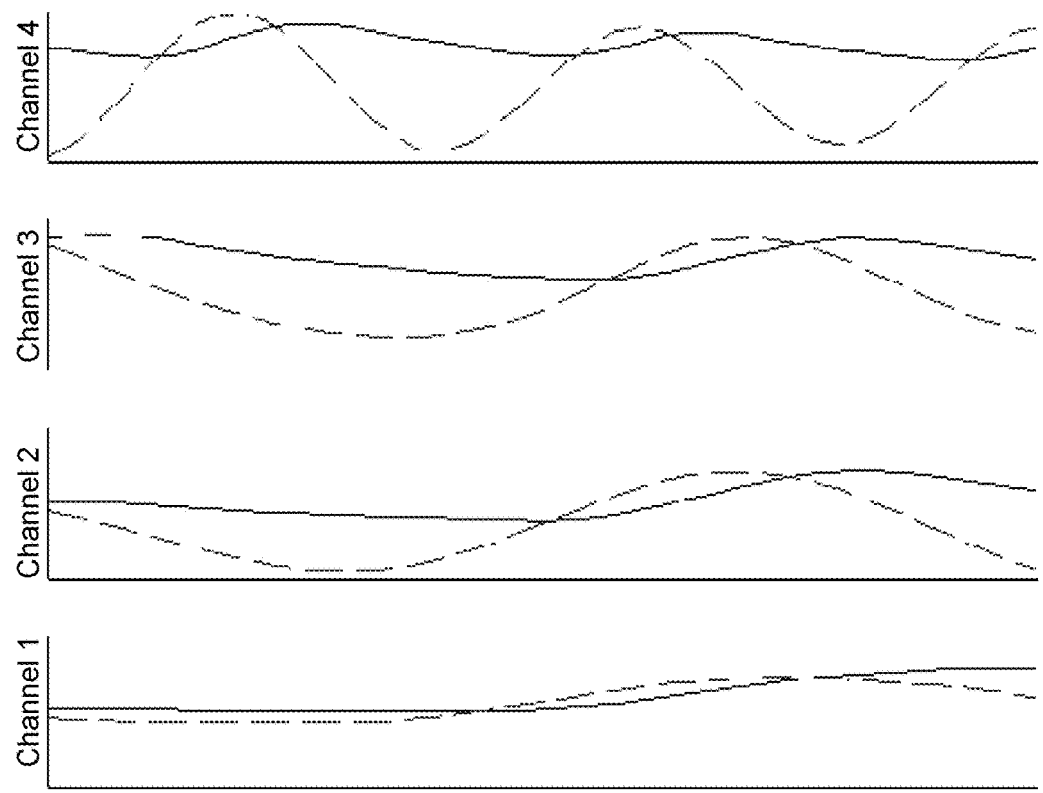
FIG. 9 shows band pass filtered and corresponding envelope signals for four adjacent electrode channels.
Figure 10:
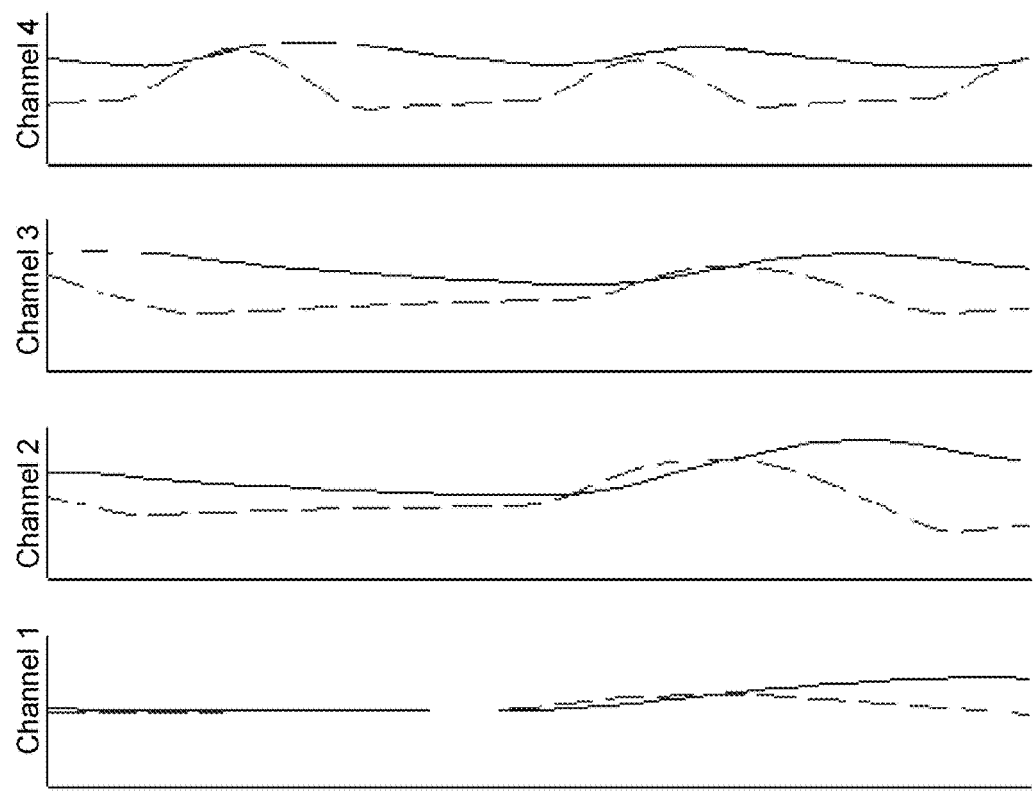
FIG. 10 shows the same envelope signals as in FIG. 9 and the first time derivatives.
Figure 11:
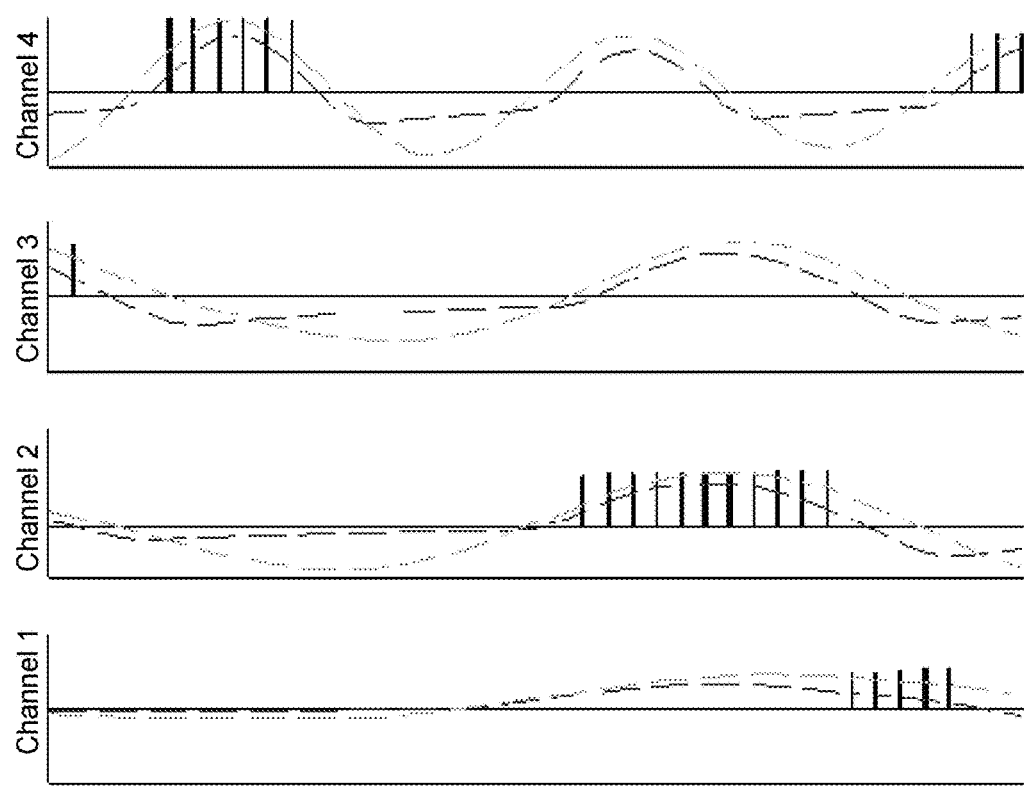
FIG. 11 shows the first time derivative signals of the signal envelopes with examples of the resulting stimulation pulse timings.

An envelope processing module 502 processes the band pass signals B in a sequence of sampling time frames, wherein for each time frame, the processing includes calculating for each band pass signal at least one signal envelope dynamic property C that is changing during the time frame. For example, the dynamic property C calculated by the envelope processing module 502 may specifically be a first-order time derivative or higher. The envelope processing module 502 can calculate the signal envelopes by halfway rectifying the band pass signals B, followed by low-pass filtering, for example with an IIR low-pass filter. Alternatively, the envelope processing module 502 can perform the envelope calculations via Hilbert transformation. The envelope signals can be designated B1, and the sampling point in time is denoted as (t), then the envelope processing module 502 can compute the first time derivative with a difference in time $\Delta t$ by $C(t)=B1(t)-B1(t-\Delta t)$. FIG. 9 shows examples of band pass filtered signals B in dashed lines and the corresponding envelope signals in solid lines for four adjacent electrode channels with the lower frequency bands on the bottom. FIG. 10 shows the same envelope signals in solid lines and the first time derivatives C in dashed lines.

A channel selection module 503 selects n band pass signals B for each time frame based on the dynamic properties C to produce the electrode stimulation signals D to the stimulation contacts. For example, the channel selection module 503 can use the first time derivative of the signal envelope to select the n electrode channels with the highest time derivative to be stimulated within a given time frame. One simple implementation selects only one electrode channel (n=1) out of the m available channels. This leads to stimulation with the highest possible resolution in time since the maximum rate for coding differences in a changing input signal is only limited by the time period of one stimulation pulse. Temporal accuracy can be further maximized by allowing n pulses in parallel for stimulation instead of stimulating sequentially.

Figure 6:
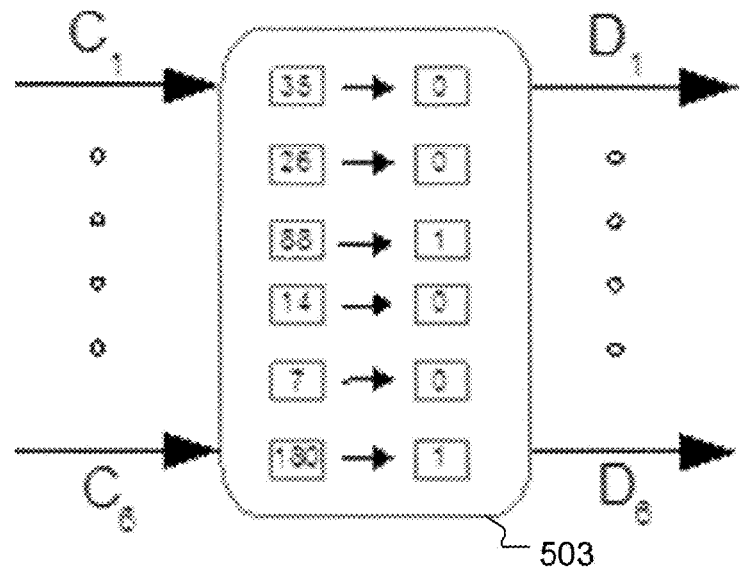
FIG. 6 shows internal functional details of the channel selection module according to one specific embodiment of the present invention.

FIG. 6 shows internal functional details of the channel selection module 503 according to one specific embodiment with m=6 input band pass channels where n=2 channels with the maximum values of the dynamic property C are selected for stimulation. The channel selection module 503 sets the output values of the selected channels to one and the remaining m-n channels are set to output values of zero (and therefore not selected for stimulation).

Figure 7:
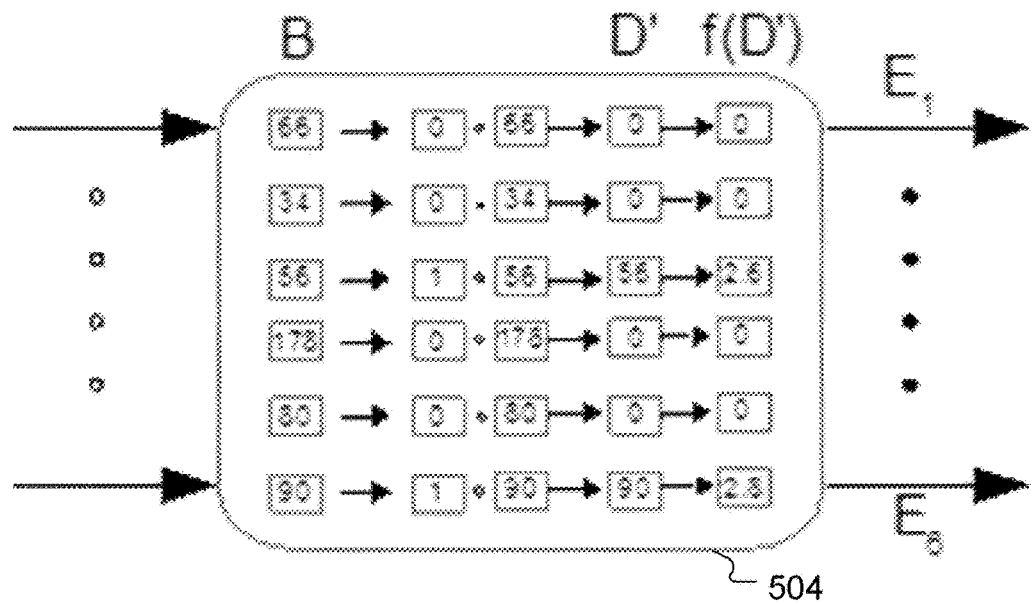
FIG. 7 shows internal functional details of the pulse scaling module according to one specific embodiment of the present invention.

A pulse scaling module 504 weights the electrode stimulation signals based on patient-specific stimulation response characteristics. FIG. 7 shows internal functional details of the pulse scaling module 504 according to one specific embodiment which first scales the D signals of the N selected channel signals with their corresponding dynamical values, e.g. $D'(t)=D(t)*B(t)$. The scaled $D'(t)$ signals are then transferred by patient-specific fitting values to individual dynamical ranges with transfer functions $f(x)$ to the patient-specific values E. In this specific example, the function $f(x)$ is $\log(1+c*x)/\log(1+c)$ with $c=10$. The pulse scaling module 504 then passes the output of these scaling operations on to the stimulation contacts as signals $E(t)=f(D'(t))$. Dynamical values used for scaling can be the band-pass signals B or signals from the calculation module, typically the envelope values B1(t), or C(t), or other derivatives in time or combination of the named signals.

Figure 8:
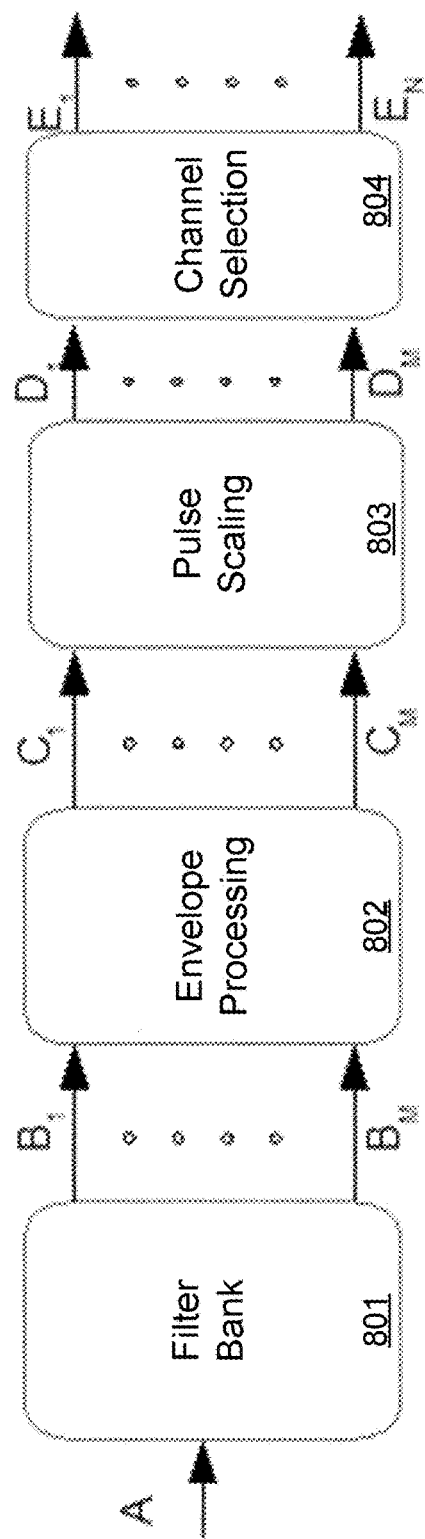
FIG. 8 shows various functional blocks in a dynamic stimulation channel selection processing system according to another embodiment of the present invention.

Other embodiments could use higher-order time derivatives or combinations of signal envelope amplitude and time derivatives as channel selection criteria in the channel selection module 503. Another embodiment is shown in FIG. 8 with an envelope processing module 802 that performs the calculation of the dynamic features (e.g. time derivatives) immediately preceding the pulse scaling module 803, and then the channel selection module 804 follows using dynamic properties of signals E.

Embodiments of the invention may be implemented in part any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A signal processing arrangement for generating electrode stimulation signals to stimulation contacts in a cochlear implant electrode array, the arrangement comprising:
   a signal filter bank configured to transform an input sound signal into a plurality of band pass signals each representing an associated frequency band of audio frequencies;
   an envelope processing module configured to process the band pass signals in a sequence of sampling time frames, wherein for each time frame, the processing includes calculating for each band pass signal at least one signal envelope higher order dynamic property that is changing during the time frame; and
   a channel selection module configured to select in each time frame, one or more of the band pass signals based on the higher order dynamic properties to produce the electrode stimulation signals to the stimulation contacts.

2. The arrangement according to claim 1, further comprising:
   a pulse scaling module configured to weight the electrode stimulation signals based on patient-specific stimulation response characteristics.

3. The arrangement according to claim 2, wherein the pulse scaling module precedes the channel selection module.

4. The arrangement according to claim 2, wherein the pulse scaling module follows the channel selection module.

5. The arrangement according to claim 1, wherein the at least one signal envelope higher order dynamic property is a first time derivative.

6. The arrangement according to claim 1, wherein the channel selection module configured to select one band pass signal for each time frame based on the higher order dynamic properties.

7. The arrangement according to claim 1, wherein the channel selection module further uses band pass signal envelope amplitude to select the one or more band pass signals.

* * * * *